United States Patent

Takeuchi

[11] 4,016,528

[45] Apr. 5, 1977

[54] MOVING TARGET DETECTOR

[75] Inventor: Yasuhito Takeuchi, Kunitachi, Japan

[73] Assignee: Hewlett-Packard Company, Palo Alto, Calif.

[22] Filed: Nov. 24, 1975

[21] Appl. No.: 634,955

[30] Foreign Application Priority Data

Dec. 23, 1974 Japan ............................. 49-147873

[52] U.S. Cl. .............................. 340/1 R; 340/3 D; 343/7.7

[51] Int. Cl.² .......................................... G01S 9/66

[58] Field of Search ............ 340/3 D, 258 A, 1 R; 343/7.7

[56] References Cited

UNITED STATES PATENTS

| 3,662,371 | 5/1972  | Lee et al. | 340/258 A |
| 3,781,773 | 12/1973 | Ravas      | 340/1 R   |
| 3,878,526 | 4/1975  | Pedersen   | 343/7.7   |

Primary Examiner—Richard A. Farley
Attorney, Agent, or Firm—Robert S. Hulse

[57] ABSTRACT

An ultrasonic echo system for detecting moving targets by processing the doppler shifted reflected signals. Signals indicative of stationary objects are suppressed by a feedback arrangement which subtracts signal components derived from stationary objects from the incoming echo signals.

5 Claims, 1 Drawing Figure

MOVING TARGET DETECTOR

BACKGROUND OF THE INVENTION

Presently, many electronic instruments exist that use the ultrasound doppler method in detecting, for example, blood flow or fetal heartbeat. These instruments generally use one of two methods to remove from an input signal describing an area of investigation the usually large signal component indicative of stationary objects within the area of investigation, and to reveal the usually weak doppler signal component indicative of moving objects within the area of investigation.

One method involves early demodulation of the input signal after receipt and sharply cutting-off the lower components of the signal after demodulation. This method avoids the problem of saturation that could be caused by the usually large stationary signal component when the input signal is amplified before demodulation, but this method requires demodulator and top-stage baseband (audio frequency) amplifier with an excellent noise figure. Noise figure (NF) is defined as follows:

$$NF = 10 \log \frac{(S/N) \text{ power, input}}{(S/N) \text{ power, output}}$$

where (S/N) represents signal-to-noise ratio.

Another method involves the use of a sharp notch filter to eliminate or remove the stationary signal component. But, such filters are expensive for they must not only suppress the carrier frequency and frequencies within about 100 Hz of the carrier frequency inherent in the input signal, but must also pass frequencies that are more than 100 Hz away from the carrier frequency.

Both of the above methods produce distortion or cross modulation and otherwise increase the overall noise figure of an instrument or system when removal of the stationary component and amplification of the weak doppler component are performed.

SUMMARY OF THE INVENTION

Thus, in accordance with the illustrated preferred embodiment of the present invention, a moving target detector system is provided which removes the stationary signal components from an input signal by means of a feedback technique, and amplifies the doppler shift signal components. This technique improves, i.e., reduces rather than increases, a system's overall noise figure.

The illustrated preferred embodiment shows a system comprising paired balanced demodulators and modulators driven by paired orthogonal carriers, paired low pass filters, and a feedback loop containing a coupling circuit and amplifier. After the input signal is demodulated, paired output signals are produced from which the doppler shift components are filtered-out and the remaining DC and low frequency (stationary) components are remodulated, fed back to the coupling circuit and subtracted from the input signal, thereby producing a resultant signal comprising essentially the doppler shift component. This resultant signal is then amplified and demodulated to remove any residual carrier component, thereby essentially suppressing the stationary components and providing the doppler shift signal components as paired orthogonal base band output signals characteristic of moving targets or objects within the area of investigation.

DESCRIPTION OF THE PREFERRED EMBODIMENT

Figure 1:
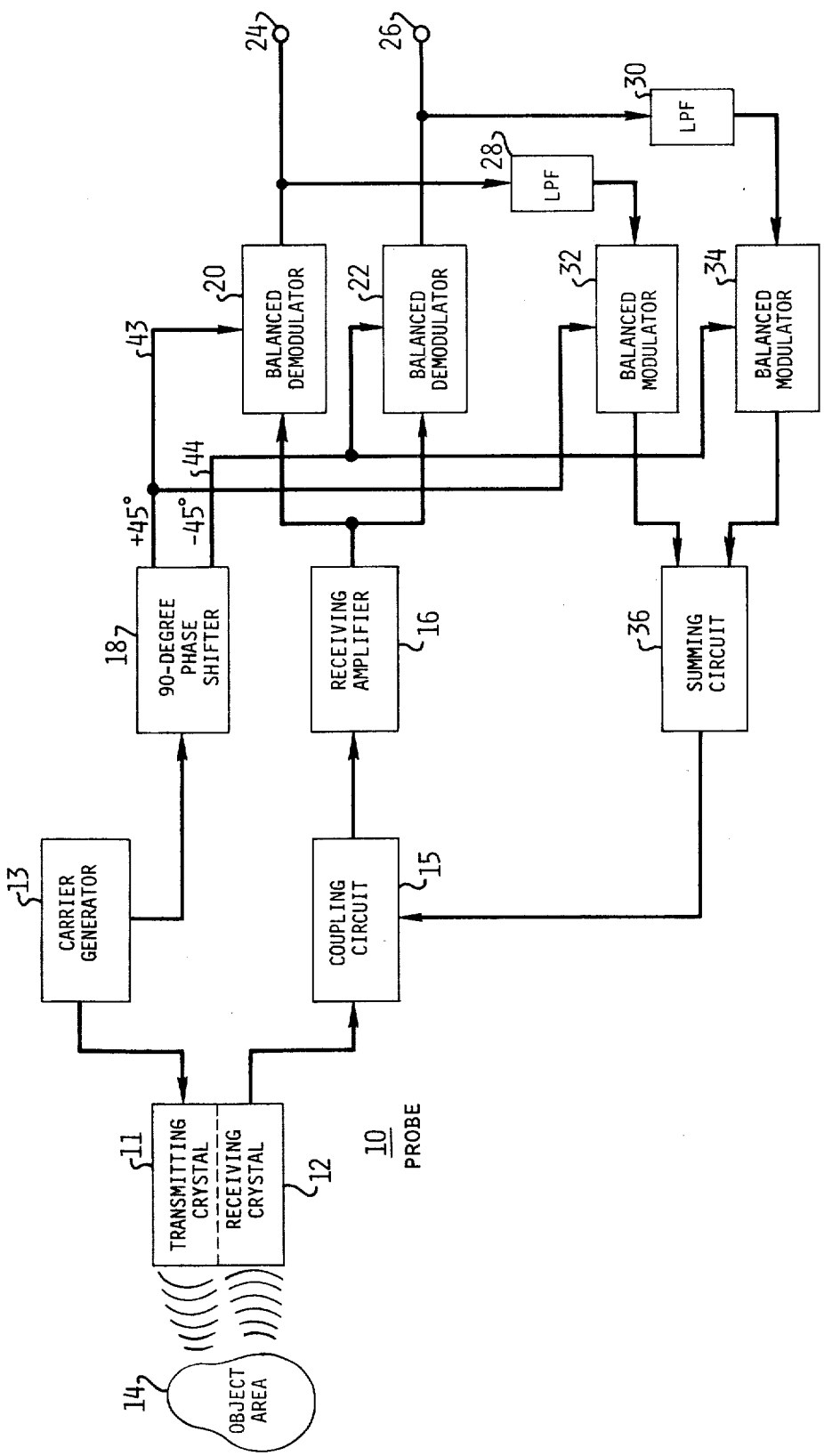
FIG. 1 is a block diagram of the system of the present invention.

FIG. 1 is a block diagram of a moving target detector system according to the preferred embodiment of the present invention. Probe 10 is a transducer or acoustic signal transmitter-receiver having a transmitting crystal 11 and receiving crystal 12. Transmitting crystal 11 is driven by carrier generator 13, producing an acoustic signal which is applied to an object area of a patient's body under investigation. The acoustic signal reflected from the object area is received by receiving crystal 12. This reflected acoustic signal comprises a carrier component, a stationary reflection component representing the signal component reflected from stationary parts of the object area, and a doppler shift component representing the signal component reflected from moving parts of the object area. The reflected acoustic signal is applied to receiving amplifier 16 through coupling circuit 15. The output of amplifier 16 is applied to a pair of balanced demodulators 20, 22. These demodulators 20, 22 are driven by paired orthogonal (i.e., 90° out of phase with respect to each other, ±45°) carrier signals 43, 44 produced by phase shifter 18. Phase shifter 18, in turn, is driven by carrier generator 13. The output signals from balanced demodulators 20, 22 represent orthogonal base-band doppler shift signals. These signals are applied to balanced modulators 32, 34 via paired low pass filters 28, 30. The filters 28, 30 serve to remove the doppler shift components of the signals. The balanced modulators 32, 34 are also driven by orthogonal carrier signals 43, 44. The output signals from modulators 32, 34 are then combined by summing circuit 36 to produce a signal having a carrier component and a stationary reflection component.

This combined or reconstructed signal is then fed back to coupling circuit 15 where the reconstructed signal is subtracted from the reflected acoustic input signal to produce a resulting signal having essentially only a doppler shift component. This resulting signal is then amplified by receiving amplifier 16 and demodulated by balanced demodulators 20, 22 to remove any residual carrier component and to produce essentially only the doppler shift component as an output signal at output terminals 24 and 26.

The following is a mathematical representation, in the form of a distributed frequency spectra around a carrier frequency produced by carrier generator 13, of the acoustic signal reflected from object area 14 and received by receiving crystal 12:

$$E_r = \sum_{i=-\infty}^{+\infty} a_i \cos \ (\omega_0 + \omega_{di}) t + \phi_i \qquad (1)$$

Where $E_r$ represents the voltage level of the signal received by the receiving crystal 12 at any instant in time $(t)$, $i = -\infty, \ldots -1, 0, +1, \ldots +\infty$, $a_i$ and $\omega_i$ are amplitude and phase, respectively of the ith component of $E_r$. $\omega_0$ = angular velocity of the carrier signal. $\omega_0 + I\omega_d$ represents the frequency of the ith component of the input signal.

Because the system is linear, formula (1) may be expressed, alternatively as:

$$E_r = E_{r_0} + E_{r_1} \qquad (2)$$

where $E_{r_0}$ represents the voltage level of the stationary components of the input signal, and $E_{r_1}$ represents the voltage level of the doppler shift components of the input signal. More specifically, $$E_{r_0} = \sum_{|i|=0}^{k} a_i \cos\{(\omega_0 + \omega_d i)t + \phi_i\} \qquad (3)$$

$$E_{r_1} = \sum_{|i|=k+1}^{\infty} a_i \cos\{(\omega_0 + \omega_d i)t + \phi_i\} \qquad (3a)$$

Absent the effect of a feedback signal applied to coupling circuit 15, the voltages of the output signals from demodulators 20 and 22 may be represented as follows:

$$D_+ = 2\left[\sum_{i=-\infty}^{+\infty} a_i \cos\{(\omega_0 + \omega_d i)t + \phi_i\}\right]\cos\omega_0 t$$

$$\approx \sum_{i=-\infty}^{+\infty} a_i \cos(\omega_d i t + \phi_i) \qquad (4)$$

$$D_- = 2\left[\sum_{i=-\infty}^{+\infty} a_i \cos\{(\omega_0 + \omega_d i)t + \phi_i\}\right]\sin\omega_0 t$$

$$\approx \sum_{i=-\infty}^{+\infty} a_i \sin(\omega_d i t + \phi) \qquad (5)$$

Alternatively, $D_+$ and $D_-$ may be expressed as follows:

$$D_+ = D_{+_0} + D_{+_1} \qquad (6)$$

$$D_- = D_{-_0} + D_{-_1} \qquad (6a)$$

where $D_{+_0}$ and $D_{-_0}$ represent base band forms of stationary components of the input signal, and $D_{+_1}$ and $D_{-_1}$ represent desired base band doppler signal components. These components are defined in greater detail following:

$$D_{+_0} = \sum_{|i|=0}^{k} a_i \cos(\omega_d i t + \phi_i) \qquad (7)$$

$$D_{-_0} = \sum_{|i|=0}^{k} a_i \sin(\omega_d i t + \phi_i) \qquad (7a)$$

$$D_{+_1} = \sum_{|i|=k+1}^{\infty} a_i \cos(\omega_d i t + \phi_i) \qquad (7b)$$

$$D_{-_1} = \sum_{|i|=k+1}^{\infty} a_i \sin(\omega_d i t + \phi_i) \qquad (7c)$$

With the base band doppler shift signals filtered out by low pass filters 28 and 30, the output of summing circuit 36 that is fed back to coupling circuit 15 may be represented as follows:

$$E_{r_{00}} = D_{+_0}\cos\omega_0 t + D_{-_0}\sin\omega_0 t \qquad (8)$$

-continued $$\approx \sum_{|i|=0}^{k} a_i \cos\{(\omega_0 + \omega_d i)t + \phi_i\}$$

The output signal produced at terminal 24 is the same as the signal produced at terminal 26 except for a 90° shift in phase. When input signal voltage $E_r$ and feedback signal voltage $E_{r_{00}}$ are applied to coupling circuit 15, the output signal voltage $D_f$ at terminal 24 or 26 may be expressed as follows:

$$D_f = D_{f_0} + D_{f_1} = DEM(E_r - AE_{r_{00}}) \qquad 9.$$

where $D_{f_0}$ represents the stationary component of the output signal, $D_{f_1}$ represents the doppler shift component of the output signal, $DEM$ represents a demodulation operator, and $A$ represents the feedback loop gain of the system.

From equation (2) and from the relationships $E_{r_{00}} = MOD(D_{f_0})$ and $DEM = MOD^{-1}$, where $MOD$ represents a modulation operator, equation (9) may be rewritten as follows:

$$D_{f_0} + D_{f_1} = DEM\{E_{r_0} - A\ MOD(D_{f_0}) + E_{r_1}\} =$$
$$DEM(E_{r_0} + E_{r_1}) - A\ DEM\{MOD(D_{f_0})\} \qquad 10.$$

Equation (10), in turn, may be rewritten as:

$$(1+A)D_{f_0} + D_{f_1} = DEM(E_{r_0} + E_{r_1}) \qquad 11.$$

which, upon grouping stationary and doppler shift components separately, produces:

$$(1 + A)D_{f_0} = DEM(E_{r_0}) \qquad 12.$$

and $$D_{f_1} = DEM(E_{r_1}) \qquad 13.$$

Hence, from equation (12), $D_{f_0}$ may be expressed as:

$$D_{f_0} = \frac{1}{1+A} DEM(E_{r_0}) = \frac{1}{1+A} D_0 \qquad (14)$$

which shows that the stationary component ($D_{f_0}$), when feedback occurs, decreases to a fraction $1/(1+A)$ of $D_0$. $D_0$ represents the stationary component when no feedback occurs. For a large feedback loop gain ($A$), therefore, the undesired stationary component of the input signal is greatly suppressed. On the other hand, as equation 13 shows, desired doppler shift components remain unchanged even for large feedback loop gain.

The doppler shift component signals that are output from terminals 24 and 26 may then be transformed, see for example the Hilbert transformation method shown by equation (15) below, and recombined to provide information about the extent and direction of movement of portions of the object area under investigation. The object area may be part of the human body, highway traffic area, or other areas.

$$H\{f(t)\} = \frac{1}{\pi}\int_{-\infty}^{+\infty} \frac{f(y)}{t-y} dy \qquad (15)$$

It should be noted that a 90° carrier phase shift produced by shifter 18 is not mandatory for the system to operate. A phase shift that results in a sufficient skew or phase difference in the carrier signals applied to demodulators 20 and 22 would be satisfactory.

I claim:

1. A system for detecting moving objects within an object area of investigation by suppressing stationary components and amplifying doppler-shift components of acoustic signals reflected from stationary and moving objects within the area of investigation, said system comprising:

carrier generator means for generating a sinusoidal input carrier signal of constant amplitude and constant frequency;

signal transmitter means connected to said carrier generator means for transmitting an acoustic signal to the object area in response to said input carrier signal;

signal receiver means responsive to acoustic signals reflected from stationary and moving objects within said object area for converting said reflected acoustic signal to an analog signal having carrier, stationary and doppler-shift components;

signal coupling means having an input terminal coupled to said signal receiver means and having a feedback terminal for subtracting feedback signals received at the feedback terminal from analog signals received at the input terminal, and for producing a resultant analog signal having primarily doppler-shift components;

phase shifter means coupled to said carrier generator means and having a pair of output terminals for producing a pair of phase-shifted carrier signals in response to said input carrier signal;

paired demodulator means each coupled to said signal coupling means and to an output terminal of said phase shifter means for producing a pair of demodulated analog signals, phase shifted with respect to each other, and having primarily doppler-shift components; and signal feedback means coupled to said paired demodulator means and to the feedback terminal of said coupling means for providing a feedback signal to said signal coupling means, said feedback signal having primarily carrier and stationary components.

2. The system of claim 1 wherein said signal feedback means comprises paired low pass filter means each connected to one of said paired demodulator means for removing doppler-shift components from the paired demodulated analog signals and producing paired analog signals having primarily stationary components.

3. The system of claim 2 wherein said signal feedback means further comprises paired modulator means, each coupled to one of said paired low pass filter means and to one of the pair of output terminals of said phase shifter means, for producing paired analog signals having primarily carrier and stationary components.

4. The system of claim 3 wherein said signal feedback means still further comprises a summing circuit means coupled to both modulator means for providing to the signal coupling means a single feedback signal having primarily carrier and stationary components.

5. The system of claim 1 wherein said system includes an amplifier means coupled to said signal coupling means and to said paired demodulator means for receiving the resultant analog signal from said signal coupling means, and amplifying and applying said signal to both demodulator means.

* * * * *